(12) United States Patent
Van Der Heide et al.

(10) Patent No.: US 9,302,965 B1
(45) Date of Patent: Apr. 5, 2016

(54) PROCESS FOR THE PREPARATION OF GLYCOLS

(71) Applicant: SHELL OIL COMPANY, Houston, TX (US)

(72) Inventors: Evert Van Der Heide, Amsterdam (NL); Govinda Subbanna Wagle, Bangalore (IN)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/781,756

(22) PCT Filed: Apr. 1, 2014

(86) PCT No.: PCT/EP2014/056524
§ 371 (c)(1),
(2) Date: Oct. 1, 2015

(87) PCT Pub. No.: WO2014/161852
PCT Pub. Date: Oct. 9, 2014

(30) Foreign Application Priority Data

Apr. 5, 2013 (EP) .................................... 13162503

(51) Int. Cl.
*C07C 29/132* (2006.01)
*C07C 29/00* (2006.01)

(52) U.S. Cl.
CPC ............... *C07C 29/132* (2013.01); *C07C 29/00* (2013.01)

(58) Field of Classification Search
CPC .............................. C07C 29/132; C07C 29/00
USPC .................................................. 568/861, 852
See application file for complete search history.

(56) References Cited

U.S. PATENT DOCUMENTS

| 2011/0160482 A1 | 6/2011 | Nagaki et al. |
| 2011/0313208 A1 | 12/2011 | Kalnes et al. |
| 2012/0172633 A1 | 7/2012 | Zhang et al. |

FOREIGN PATENT DOCUMENTS

| CN | 103731258 | 4/2014 |
| WO | 2012174087 | 12/2012 |
| WO | 2013015955 | 1/2013 |

OTHER PUBLICATIONS

Zhang, Ji, et al.: Direct Catalytic Conversion of Cellulose into Ehtylene Glycol Using Nickel-Promoted Tungsten Carbide Catalysts, Biomass Conversion, Angew. Chemie. Int. Ed. 2008, 47, pp. 8510-8513.
Tai, Zhijun, et al.: Temperature-controlled phase-transfer catalysis for ethylene glycol production from cellulose, Chem. Commun., 2012, 48, pp. 7052-7054.
Lilu, Yue, et al.: Tungsten Trioxide Promoted Selective Conversion of Cellulose into Propylene Glycol and Ethylene Glycol on a Ruthenium Catalyst, Angewandte Chemie International Edition, vol. 51, Issue 13, pp. 3249-3253, Mar. 26, 2012.
Dedsuksophon, W., et al.: Hydrolysis/ dehydration/ aldol-condensation/ hydrogenation of lignocellulosic biomass and biomass-derived carbohydrates in the presence of Pd/WO3-ZrO2 in a single reactor, Bioresource Technology 102, 2 (2011) pp. 2040-2046.
International Search Report dated Apr. 14, 2014 for PCT/EP2014/056524 filed Apr. 1, 2014.

*Primary Examiner* — Elvis O Price

(57) ABSTRACT

The invention provides a process for the preparation of ethylene glycol and 1,2-propylene glycol from starting material comprising one or more saccharides, by contacting said starting material with hydrogen in a reactor in the presence of a solvent and a catalyst system with catalytic hydrogenation abilities, wherein the process comprises the steps of: i) introducing a first portion of the starting material into the reactor such that the initial concentration of the saccharide in the solvent in the reactor is no more than 2 wt %; ii) allowing at least 90 wt % of the saccharide in the first portion of the starting material to react; iii) subsequently adding further portions of starting material to the reactor over time; and removing reaction product from the reactor.

6 Claims, No Drawings

PROCESS FOR THE PREPARATION OF GLYCOLS

PRIORITY CLAIM

The present application is a National Stage §371 application of PCT/EP2014/056524, filed Apr. 1, 2014, which claims priority from European Patent Application EP13162503.0 filed Apr. 5, 2013, each of which are hereby incorporated by reference in their entirety.

FIELD OF THE INVENTION

The present invention relates to a process for the preparation of ethylene and propylene glycols from saccharide-containing feedstock.

BACKGROUND OF THE INVENTION

Ethylene glycol and propylene glycol are valuable materials with a multitude of commercial applications, e.g. as heat transfer media, antifreeze, and precursors to polymers, such as PET. Ethylene and propylene glycols are currently made on an industrial scale by hydrolysis of the corresponding alkylene oxides, which are the oxidation products of ethylene and propylene, produced from fossil fuels.

In recent years, increased efforts have focussed on producing glycols from renewable feedstocks, such as sugar-based materials. The conversion of sugars to glycols can be seen as an efficient use of the starting materials with the oxygen atoms remaining intact in the desired product.

Current methods for the conversion of saccharides to sugars revolve around a hydrogenation/hydrogenolysis process as described in Angew. Chem. Int. Ed. 2008, 47, 8510-8513. Continuous processes for generating at least one polyol from a saccharide-containing feedstock are described in WO 2013/015955 and CN 103731258A. A process for the co-production of bio-fuels and glycols is described in WO 2012/174087.

An important aim in this area is the provision of a process that is high yielding in desirable products, such as ethylene glycol and propylene glycol, and that can be carried out on a scale that makes it industrially viable. A key consideration, therefore, is the level of dilution of the catalytic process. Carrying out the process at high levels of dilution can lead to inefficiencies and will add to the difficulties in separating the desired products.

Although acceptable conversion levels to the desired products are now possible for the catalytic conversion of saccharides to glycols, these are generally achieved at low concentrations of saccharides in the catalytic reactors. In general, the use of higher concentrations of saccharides leads to reduced overall yields.

It would be desirable, therefore, to provide a process for the catalytic conversion of saccharides to glycols in which higher concentrations of saccharides can be used while maintaining acceptable yields of the desirable glycols.

SUMMARY OF THE INVENTION

Accordingly, the present invention provides a process for the preparation of ethylene glycol and 1,2-propylene glycol from starting material comprising one or more saccharides, by contacting said starting material with hydrogen in a reactor in the presence of a solvent and a catalyst system with catalytic hydrogenation abilities, wherein the process comprises the steps of:

i) introducing a first portion of the starting material into the reactor such that the initial concentration of the saccharide in the solvent in the reactor is no more than 2 wt %;
ii) allowing at least 90 wt % of the saccharide in the first portion of the starting material to react;
iii) subsequently adding further portions of starting material to the reactor over time; and
iv) removing reaction product from the reactor.

DETAILED DESCRIPTION OF THE INVENTION

The present inventors have surprisingly found that the reduction in overall yield obtained when carrying out the catalytic conversion of saccharides to glycols with saccharide solutions, suspensions or slurries at higher concentrations can be reduced by using a procedure in which an initial portion of starting material is added to the reactor and allowed to react to near completion before any further material is added.

The starting material for the subject process comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof. If the starting material comprises oligosaccharides or polysaccharides, it is preferable that it is subjected to pre-treatment before being fed to the reactor in a form that can be converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the starting material comprises one or more saccharide selected from the group consisting of glucose, sucrose and starch. Said saccharide is suitably present as a solution, a suspension or a slurry in the solvent.

The solvent present in the reactor may be water or a $C_1$ to $C_6$ alcohol or mixtures thereof. Preferably, the solvent is water. If the starting material is provided to the reactor as a solution, suspension or slurry in a solvent, said solvent is also suitably water or a $C_1$ to $C_6$ alcohol or mixtures thereof. Preferably, both solvents are the same. More preferably, both solvents comprise water. Most preferably, both solvents are water.

The catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the reactor is heated to a temperature within these limits before addition of any starting material and is maintained at such a temperature until all reaction is complete.

The pressure in the reactor is suitably at least 1 MPa, preferably at least 2 MPa, more preferably at least 3 MPa. The pressure in the reactor is suitably at most 16 MPa, more preferably at most 12 MPa, more preferably at most 10 MPa, even more preferably at most 8 MPa, most preferably at most 6 MPa. Preferably, the reactor is pressurised to a pressure within these limits by addition of hydrogen before addition of any starting material and is maintained at such a pressure until all reaction is complete. This can be achieved by subsequent addition of hydrogen.

The process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents. It may also be suitable to add further hydrogen to the reactor as the reaction proceeds.

The reactor in the present invention may be any suitable reactor known in the art.

In step i) of the process of the present invention, a first portion of starting material is introduced into the reactor such that the initial concentration of sugar in the solvent in the reactor is no more than 2 wt %. The solvent includes any solvent already present in the reactor as well as any solvent present in the slurry, solution or suspension of the starting material. The initial concentration is preferably no more than 1.8 wt %, more preferably no more than 1.5 wt %, more preferably no more than 1.3 wt %, more preferably no more than 1.0 wt %, even more preferably no more than 0.8 wt %, most preferably no more than 0.5 wt %.

The initial concentration of the sugar in the solvent in the reactor is suitable at least 0.1 wt %, preferably at least 0.2 wt %, more preferably at least 0.3 wt %.

In step ii), at least 90 wt % of the saccharide in the first portion of the starting material is allowed to react. Preferably, at least 95 wt %, more preferably at least 98 wt %, even more preferably at least 99 wt %, most preferably substantially 100 wt % is allowed to react before further portions of starting material can be added in step iii).

The process may be carried out as a batch process or as a continuous flow process.

In one embodiment of the invention, the process is a batch process. In said process, after initial loading of catalyst and, optionally, solvent, the reactor is heated and pressurised with hydrogen and then the first portion of starting material is introduced into the reactor and allowed to react until at least 90 wt % of the saccharide has reacted.

In this embodiment of the invention, further portions of starting material are then added to the reactor over time until the total concentration of saccharide in the solvent in the reactor is at least 5 wt %. Total concentration as used herein refers to the concentration calculated as a weight percentage of the total amount of saccharide added in the total amount of solvent present in the reactor. The total amount of saccharide added corresponds to the sum total of the amount of saccharide added in the first portion and all further portions. The total amount of solvent in the reactor includes any solvent already present in the reactor as well as any solvent present in the slurry, solution or suspension of the starting material. Preferably, further portions of starting material are added to the reactor over time until the total concentration of sugar in the solvent in the reactor is at least 7 wt %, more preferably at least 8 wt %, even more preferably at least 10 wt %. Suitably the total concentration of sugar in the solvent is no higher than 30 wt %, preferably no higher than 25 wt %.

In this embodiment of the invention, adding further portions of starting material may occur in a continuous manner or the portions may be added in a discontinuous manner with time elapsing between the end of the addition of one portion and the start of the addition of the next portion. In the embodiment of the invention wherein the portions are added in a discontinuous manner, the number and size of each portion will be dependent on the scale of the reactor. Preferably, the total number of portions including the first portion is no less than 5, more preferably no less than 8, even more preferably no less than 10. The amount of time over which each portion is added and the time to be elapsed between the end of the addition of one portion and the start of the addition of the next portion will also depend on the scale of the reactor. Preferably, the time to be elapsed between the end of the addition of one portion and the start of the addition of the next portion will be greater than the amount of time over which each portion is added.

In this embodiment of the invention, wherein the process is a batch process, after addition of all of the portions of the starting material, the reaction may then be allowed to proceed to completion for a further period of time. The reaction product will then be removed from the reactor in step iv).

In the embodiment of the invention wherein the process is carried out as a continuous flow process, after initial loading of catalyst and, optionally, solvent, the reactor is heated and pressurised with hydrogen and then the first portion of starting material is introduced into the reactor and allowed to react until at least 90 wt % of the saccharide has reacted. Further portions of starting material are then provided to the reactor. Reaction product is removed from the reactor in a continuous manner.

In this embodiment, the starting material is suitably a saccharide feedstock comprising at least 1 wt % saccharide as a solution, suspension or slurry in a solvent. Preferably, said saccharide feedstock comprises at least 2 wt %, more preferably at least 5 wt %, even more preferably at least 10 wt %, most preferably at least 20 wt % saccharide in a solvent. Suitably, the saccharide feedstock contains no more than 50 wt %, preferably no more than 40 wt % saccharide in a solvent.

The present invention is further illustrated in the following Examples.

EXAMPLES

In each of the following examples, yields of monoethylene glycol (MEG), monopropylene glycol (MPG) and 1,2-butanediol (1,2-BDO) were quantified by GC-FID, applying a CPSil-5 column and are shown in Tables 1 to 3.

Example 1

0.3 g of glucose (portion 1) was dissolved in 30 ml of deionised water and charged into a 60 ml autoclave equipped with a gas stirrer and hydrogen supply along with 0.5 g of a W(10.88)-Ni(3.63)-Pt(0.05)/ZrO$_2$ catalyst and 0.5 g of a Ru(1.0)/SiO$_2$ catalyst. The autoclave was closed, the gas phase was replaced by nitrogen, then by hydrogen and the autoclave was pressurised to 3000 kPa (absolute). The autoclave was stirred at 1450 rpm, heated to 195° C. in 12-15 minutes and kept at 195° C. and 8500 kPa (absolute) for 5 minutes. The reactor was then cooled to room temperature over 15 minutes, depressurised and opened. A liquid sample of 0.3 ml was taken for analysis. 1.0 g glucose was added (portion 2), and the procedure was repeated, with a 10 minute reaction time at 195° C. Three more lots of glucose (portions 3, 4 and 5) were added following the same procedure. Finally, portion 6, comprising 1.7 g of glucose was added and the reaction was continued for 30 minutes. The total amount of glucose added to 30 ml water was 6 gram, corresponding to a total concentration of 20 wt % glucose. The total reaction time was 75 minutes at 195° C.

Example 2

The procedure of Example 1 was repeated, with the difference that 0.25 g of a W(10.88)-Ni(3.63)-Pt(0.05)/ZrO$_2$ catalyst and 0.25 g of a Ru(1.0)/SiO$_2$ catalyst were used and portions 2 to 5 each contained 0.5 g of glucose. The total amount of glucose (portions 1 to 6) added to 30 ml water was 3 g, corresponding to a total concentration of 10 wt % glucose.

Example 3

15 ml of deionised water, 0.5 g of a W(10.88)-Ni(3.63)-Pt(0.05)/ZrO$_2$ catalyst and 0.5 g of a Ru(1.0)/SiO$_2$ catalyst were charged into a 60 ml autoclave, equipped with a gas stirrer and hydrogen supply. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). 1.5 ml of a 40 wt % glucose solution in water was pumped into the autoclave every nine minutes at a rate of 5 ml per minute until 10 portions had been added. After the addition of the tenth portion, the autoclave was maintained for an additional 10 minutes at 195° C. The total amount of glucose added was 6 g, corresponding to a total concentration of 20 wt % glucose. The total reaction time was 100 minutes at 195° C.

Example 4

20 ml of deionised water, 0.250 g of a W(10.88)-Ni(3.63)-Pt(0.05)/ZrO$_2$ catalyst and 0.250 g of a Ru(1.0)/SiO$_2$ catalyst were charged into a 60 ml autoclave, equipped with a gas stirrer and hydrogen supply. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). 1.0 ml of a 30 wt % glucose solution in water was pumped into the autoclave every nine minutes at a rate of 5 ml per minute until 10 portions had been added. After the addition of the tenth portion, the autoclave was maintained for an additional 10 minutes at 195° C. The total amount of glucose added was 3 g, corresponding to a total concentration of 10 wt % glucose. The total reaction time was 100 minutes at 195° C.

Example 5 (Comparative)

6.0 g of glucose were dissolved in 30 ml of deionised water and charged into a 60 ml autoclave, equipped with a gas stirrer and hydrogen supply along with 0.200 g of a W(10.88)-Ni(3.63)-Pt(0.05)/ZrO$_2$ catalyst and 0.100 g of a Ru(1.0)/SiO$_2$ catalyst. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). The autoclave was maintained at this temperature and pressure for 75 minutes. The reactor was then cooled to room temperature over 15 minutes, depressurized, opened, and a liquid sample of 0.3 ml was taken for analysis.

Example 6 (Comparative)

Example 5 was repeated with 0.200 g of a W (10.88)-Ni (3.63)-Pt(0.05)/ZrO$_2$ catalyst and 0.200 g of a Ru(1.0)/SiO$_2$ catalyst.

Example 7

15 ml of deionised water, 0.500 g of a W(10.88)-Ni(3.63)-Pt(0.05)/ZrO$_2$ catalyst and 0.500 g of a Ru(1.0)/SiO$_2$ catalyst were charged into a 60 ml autoclave, equipped with a gas stirrer and hydrogen supply. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). A 40 wt % solution of glucose (total 15.5 ml) in water was added in 28 portions, with each portion being added over one minute, and the reaction being allowed to proceed for 3 minutes between each addition. The details of each portion are shown in Table 4. The reaction was continued for a further 60 minutes after the additions were completed. The total amount of glucose added was 6 gram, corresponding to a total concentration of 20 wt % glucose. The total reaction time was 170 minutes at 195° C.

Example 8

Example 7 was repeated using 0.0750 g of a W (10.88)-Ni (3.63)-Pt(0.05)/ZrO$_2$ catalyst and 0.0750 g of a Ru(1.0)/SiO$_2$ catalyst and with 5 minutes reaction time after the addition of each portion. The details of quantity of different lots are shown in Table 5.

Example 9

Example 7 was repeated using 0.100 g of a W(10.88)-Ni (3.63)-Pt(0.05)/ZrO$_2$ catalyst and 0.050 g of a Ru(1.0)/SiO$_2$ catalyst with 5 minutes reaction time after addition of each portion. The details of quantity of different lots are shown in Table 5.

Example 10

Example 7 was repeated using 0.050 g of a W(10.88)-Ni (3.63)-Pt(0.05)/ZrO$_2$ catalyst and 0.100 g of a Ru(1.0)/SiO$_2$ catalyst with 5 minutes reaction time after addition of each lot. The details of quantity of different lots are shown in Table 5.

Example 11 (Comparative)

0.3 g of glucose was dissolved in 30 ml of deionised water charged into a 60 ml autoclave, equipped with a gas stirrer and hydrogen supply, along with 0.025 g of a W(10.88)-Ni(3.63)-Pt(0.05)/ZrO$_2$ catalyst and 0.025 g of a Ru(1.0)/SiO$_2$ catalyst. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). The temperature and pressure were maintained for 75 minutes. The reactor was then cooled to room temperature over 15 minutes, depressurized, opened and a liquid sample of 0.3 ml was taken for analysis.

Example 12 (Comparative)

3.0 g of glucose was dissolved in 30 ml of deionised water and charged into a 60 ml autoclave, equipped with a gas stirrer and hydrogen supply, along with 0.250 g of a W(10.88)-Ni (3.63)-Pt(0.05)/ZrO$_2$ catalyst and 0.250 g of a Ru(1.0)/SiO$_2$ catalyst. The autoclave was closed, the gas phase replaced by nitrogen, then by hydrogen and the autoclave was pressurised to 3000 kPa (absolute). The autoclave was stirred at 1450 rpm, heated to 195° C. in 12-15 minutes and the pressure increased to 8500 kPa (absolute). The temperature and pressure were maintained for 75 minutes. The reactor was then cooled to room temperature over 15 minutes, depressurized, opened and a sample was taken for analysis.

Example 13 (Comparative)

Example 12 was repeated using 6.0 g of glucose dissolved in 30 ml of deionised water, 0.500 g of a W(10.88)-Ni(3.63)-Pt(0.05)/ZrO$_2$ catalyst and 0.500 g of a Ru(1.0)/SiO$_2$ catalyst.

TABLE 1 glycol yields in Example 1

| cumulative glucose concentration (wt %) | MEG yield (%) | MPG yield (%) | 1,2-BDO yield (%) |
|---|---|---|---|
| 1.0 | 7.7 | 6.6 | 0.8 |
| 4.3 | 26.8 | 7.7 | 2.0 |
| 7.7 | 29.3 | 6.7 | 2.3 |
| 11.0 | 29.2 | 6.3 | 2.7 |
| 14.3 | 27.8 | 6.0 | 2.8 |
| 20.0 | 26.5 | 6.8 | 3.7 |

TABLE 2 glycol yields in Example 2

| cumulative glucose concentration (wt %) | MEG yield (%) | MPG yield (%) | 1,2-BDO yield (%) |
|---|---|---|---|
| 1.0 | 19.4 | 6.4 | 0.6 |
| 2.7 | 30.9 | 7.2 | 1.4 |
| 4.3 | 33.8 | 6.8 | 1.8 |
| 6.0 | 34.9 | 6.6 | 2.1 |
| 7.7 | 33.8 | 6.7 | 2.4 |
| 10.0 | 32.9 | 7.2 | 2.8 |

TABLE 3 glycol yields in Examples 3 to 13

| Example | Yield of MEG (%) | Yield of MPG (%) | Yield of 1,2-BDO (%) |
|---|---|---|---|
| 3 | 30.0 | 5.5 | 3.0 |
| 4 | 33.0 | 5.0 | 2.0 |
| 5* | 3.8 | 0.3 | 0.3 |
| 6* | 11.0 | 2.0 | 2.0 |
| 7 | 30.0 | 8.0 | 2.6 |
| 8 | 25.0 | 4.0 | 3.2 |
| 9 | 23.0 | 2.7 | 2.0 |
| 10 | 22.0 | 4.7 | 3.7 |
| 11* | 42.9 | 11.7 | 4.8 |
| 12* | 22.0 | 7.0 | 4.5 |
| 13* | 14.5 | 5.0 | 4.0 |

*comparative

TABLE 4 addition of portions in Example 7

| Portion number | Time of addition in minutes start | Time of addition in minutes finish | Vol (ml) |
|---|---|---|---|
| 1 | 0 | 1 | 0.3846 |
| 2 | 4 | 5 | 0.3945 |
| 3 | 8 | 9 | 0.4046 |
| 4 | 12 | 13 | 0.4150 |
| 5 | 16 | 17 | 0.4256 |
| 6 | 20 | 21 | 0.4365 |
| 7 | 24 | 25 | 0.4477 |
| 8 | 28 | 29 | 0.4592 |
| 9 | 32 | 33 | 0.4710 |
| 10 | 36 | 37 | 0.4830 |
| 11 | 40 | 41 | 0.4954 |
| 12 | 44 | 45 | 0.5081 |
| 13 | 48 | 49 | 0.5212 |
| 14 | 52 | 53 | 0.5345 |
| 15 | 56 | 57 | 0.5482 |
| 16 | 60 | 61 | 0.5623 |
| 17 | 64 | 65 | 0.5767 |
| 18 | 68 | 69 | 0.5915 |
| 19 | 72 | 73 | 0.6067 |
| 20 | 76 | 77 | 0.6222 |
| 21 | 80 | 81 | 0.6382 |
| 22 | 84 | 85 | 0.6545 |
| 23 | 88 | 89 | 0.6713 |
| 24 | 92 | 93 | 0.6885 |
| 25 | 96 | 97 | 0.7062 |
| 26 | 100 | 101 | 0.7243 |
| 27 | 104 | 105 | 0.7429 |
| 28 | 108 | 109 | 0.7619 |
| Total (Vol) | | | 15.4763 |

TABLE 5 addition of portions in Examples 8 to 10

| Portion number | Time of addition in minutes start | Time of addition in minutes finish | Vol (ml) |
|---|---|---|---|
| 1 | 0 | 1 | 0.3846 |
| 2 | 6 | 7 | 0.3945 |
| 3 | 12 | 13 | 0.4046 |
| 4 | 18 | 19 | 0.4150 |
| 5 | 24 | 25 | 0.4256 |
| 6 | 30 | 31 | 0.4365 |
| 7 | 36 | 37 | 0.4477 |
| 8 | 42 | 43 | 0.4592 |
| 9 | 48 | 49 | 0.4710 |
| 10 | 54 | 55 | 0.4830 |
| 11 | 60 | 61 | 0.4954 |
| 12 | 66 | 67 | 0.5081 |
| 13 | 72 | 73 | 0.5212 |
| 14 | 78 | 79 | 0.5345 |
| 15 | 84 | 85 | 0.5482 |
| 16 | 90 | 91 | 0.5623 |
| 17 | 96 | 97 | 0.5767 |
| 18 | 102 | 103 | 0.5915 |
| 19 | 108 | 109 | 0.6067 |
| 20 | 114 | 115 | 0.6222 |
| 21 | 120 | 121 | 0.6382 |
| 22 | 126 | 127 | 0.6545 |
| 23 | 132 | 133 | 0.6713 |
| 24 | 138 | 139 | 0.6885 |
| 25 | 144 | 145 | 0.7062 |
| 26 | 150 | 151 | 0.7243 |
| 27 | 156 | 157 | 0.7429 |
| 28 | 162 | 163 | 0.7614 |
| Total (Vol) | | | 15.4758 |

What is claimed is:

1. A process for the preparation of ethylene glycol and 1,2-propylene glycol from starting material comprising one or more saccharides, by contacting said starting material with hydrogen in a reactor in the presence of a solvent and a catalyst system with catalytic hydrogenation abilities, wherein the process comprises the steps of:
   i) introducing a first portion of the starting material into the reactor such that the initial concentration of the saccharide in the solvent in the reactor is no more than 2 wt %;
   ii) allowing at least 90 wt % of the saccharide in the first portion of the starting material to react;
   iii) subsequently adding further portions of starting material to the reactor over time; and
   iv) removing reaction product from the reactor.

2. A process according to claim 1, wherein the catalyst system comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

3. A process according to claim 1, wherein the process is a batch process, wherein in step iii), further portions are added until the total concentration of saccharide in the solvent in the reactor is at least 5 wt %; and wherein in step iv) the reaction product is removed from the reactor after the reaction is complete.

4. A process according to claim 1, wherein the process is a continuous flow process and the reaction product is removed from the reactor in step iv) in a continuous manner.

5. A process according to claim 1, wherein a first portion of the starting material is introduced into the reactor such that the initial concentration of the saccharide in the solvent in the reactor is no more than 1 wt %.

6. A process according to claim 1, wherein the starting material comprises one or more saccharide selected from the group consisting of glucose, sucrose and starch.

* * * * *